United States Patent [19]

Gruetzke et al.

[11] Patent Number: 5,646,038
[45] Date of Patent: Jul. 8, 1997

[54] PROCESS FOR BLEACHING SURFACTANT SOLUTIONS

[75] Inventors: Juergen Gruetzke, Bochum; Stefan Schmidt, Haltern, both of Germany

[73] Assignee: Huels Aktiengesellschaft, Marl, Germany

[21] Appl. No.: 527,919

[22] Filed: Sep. 14, 1995

[30] Foreign Application Priority Data

Sep. 14, 1994 [DE] Germany .................... 44 32 621.1

[51] Int. Cl.$^6$ ............................................. D06M 16/00
[52] U.S. Cl. ............................................. 435/264; 8/101
[58] Field of Search ............................ 435/262.5, 263, 435/264

[56] References Cited

U.S. PATENT DOCUMENTS

| | | | |
|---|---|---|---|
| Re. 32,672 | 5/1988 | Huth | 435/264 |
| 4,421,668 | 12/1983 | Cox | 435/264 |
| 4,430,243 | 2/1984 | Bragg | 252/91 |
| 4,481,129 | 11/1984 | Oakes | 252/186.41 |
| 4,620,935 | 11/1986 | Baxter | 252/99 |
| 4,762,917 | 8/1988 | McDaniel, Jr. et al. . | |
| 4,933,103 | 6/1990 | Aoyagi | 252/186.38 |
| 5,206,357 | 4/1993 | Schmidt . | |
| 5,227,480 | 7/1993 | Oberholz et al. . | |
| 5,273,896 | 12/1993 | Pedersen | 435/264 |
| 5,330,677 | 7/1994 | Sotoya | 252/186.38 |
| 5,356,555 | 10/1994 | Huth | 435/264 |
| 5,362,647 | 11/1994 | Cook | 435/264 |
| 5,420,262 | 5/1995 | Schmidt . | |
| 5,461,144 | 10/1995 | Kahsnitz et al. . | |
| 5,521,091 | 5/1996 | Cook | 435/264 |
| 5,527,362 | 6/1996 | Cole | 8/111 |
| 5,542,950 | 8/1996 | Cole | 8/107 |

FOREIGN PATENT DOCUMENTS

| | | |
|---|---|---|
| 0 165 721 | 12/1985 | European Pat. Off. . |
| 0 306 652 | 3/1989 | European Pat. Off. . |
| 0 388 857 | 9/1990 | European Pat. Off. . |
| 0 526 710 | 2/1993 | European Pat. Off. . |
| 41 01 252 | 7/1992 | Germany . |
| 42 18 073 | 12/1993 | Germany . |
| WO93/13113 | 7/1993 | WIPO . |

*Primary Examiner*—Carolyn Paden
*Attorney, Agent, or Firm*—Oblon, Spivak, McClelland, Maier & Neustadt, P.C.

[57] ABSTRACT

The invention relates to a process for bleaching aqueous surfactant solutions using hydrogen peroxide, specific decomposition of the unreacted hydrogen peroxide and/or oxidizing secondary products formed therefrom being performed using enzymes. The reaction proceeds under very mild conditions and leads to extremely pale, low-odor products.

13 Claims, No Drawings

PROCESS FOR BLEACHING SURFACTANT SOLUTIONS

BACKGROUND OF THE INVENTION

1. Field of the Invention

The invention relates to a process for bleaching aqueous surfactant solutions using hydrogen peroxide in which in a first process step the actual bleaching is carried out at an alkaline pH in the presence of inorganic additives which act as decomposition inhibitors for hydrogen peroxide and in a second process step specific decomposition of the unreacted hydrogen peroxide and/or oxidizing secondary products formed therefrom is performed using enzymes.

The process is of interest in particular for surfactant solutions which contain discolorations due to their preparation, which discolorations must be bleached to give pale-colored products before use in formulations for the washing and cleaning sector, including personal care applications. This relates in particular, e.g., to alkyl polyglycosides.

Alkyl polyglycosides are prepared from natural raw materials and are non-toxic and readily degradable surface-active materials. They are therefore used as detergents and cleaning agents and as emulsifiers and dispersants. However, they only have the desired surface-active properties when the alkyl groups have at least 8 C atoms. The alkyl polyglycosides in the context of this invention comply with the formula

in which R' represents a linear or branched, saturated or unsaturated aliphatic alkyl radical having 8 to 18 carbon atoms or mixtures thereof and Z represents a polyglycosyl radical having an average value for n of 1.1 to 3 hexose or pentose units or mixtures thereof.

Preference is given to alkyl polyglycosides having alkyl radicals having 12 to 16 carbon atoms and to a polyglycosyl radical having an average value for n of 1.1 to 2. Particular preference is given to alkyl polyglycosides having a polyglycosyl radical having an average value for n of 1.1 to 1.4.

The preferred polyglycosyl radical is the polyglucosyl radical.

2. Description of the Prior Art

Alkyl polyglycosides having long-chain alkyl groups are generally prepared by single-stage or multistage syntheses. A single-stage preparation process is described, inter alia, in DE-A-41 01 252.

A two-stage preparation process is specified, for example, in EP-A-0 306 652, according to which a n-butyl glycoside is first prepared by glycosidation with n-butanol and the desired long-chain alkyl polyglycoside is thereupon prepared by transglycosidation with a long-chain alcohol.

When the reaction is complete, the alkyl polyglycosides present are dissolved in long-chain alcohols. These alcohols must then be separated off if it is desired to obtain products which give a clear solution in water.

The aqueous alkyl polyglycoside(s) solutions thus obtained are still too dark for high aesthetic requirements and must generally be subjected to bleaching.

There are numerous references in the literature as to how the bleaching can be carried out. Thus Staley (EP 0 165 721) describes a process for bleaching using hydrogen peroxide, sulphur dioxide, ozone or peracids. As no control or adjustment of the pH is provided, the bleaching results are unsatisfactory. Moreover, in this manner, by-products can be formed to an undesired extent, some of which also have a pronounced inherent odor.

Other bleaching methods such as catalytic hydrogenation (U.S. Pat. No. 4,762,918, Staley), reaction with borohydride (EP 0 388 857, Kao) and irradiation with UV light (EP 0 526 710, Hüls) have proven to be insufficiently effective.

Bleaching in the presence of bleach boosters such as alkaline earth metal ions or alkali metal silicates (WO 93 13 113, Henkel) using hydrogen peroxide does give significantly better bleaching results but it is difficult to obtain products free from hydrogen peroxide under these conditions. Residual amounts of oxidizing agents must be avoided at any rate, since they effect, inter alia, the decomposition of additives in alkyl polyglycoside(s)-containing formulations. The proposal, solving the problem of residual hydrogen peroxide bleaching in the presence of transition metal compounds (DE 42 18 073, Henkel), is likewise unconvincing. The then accelerated catalytic decomposition of hydrogen peroxide to give oxygen during the bleaching reaction decreases the available amount of hydrogen peroxide. The bleaching result is thus clearly impaired and made less effective.

The object was therefore to find a very simple process by which hydrogen peroxide which has not reacted during bleaching and/or oxidizing secondary products formed therefrom are decomposed to the required extent in concentrated surfactant solutions.

SUMMARY OF THE INVENTION

The invention therefore relates to a process for bleaching concentrated aqueous surfactant solutions, characterized in that in a first step an oxidizing bleaching is performed using hydrogen peroxide as bleaching agent in the presence of stabilizers and if appropriate after an intermediate preliminary peroxide decomposition using transition metals and/or transition metal compounds on a catalyst bed, and then in a second step excess unreacted bleaching agent and/or oxidizing secondary products resulting therefrom are eliminated by addition of catalytic enzymes.

It is completely surprising in this context that this enzymatically catalyzed reaction proceeds exclusively in the desired way in such an outstanding manner in these highly concentrated and thus extremely low-water solutions, i.e. solutions having low water activity, and in the relatively high viscosities in the presence of the stabilizer.

DESCRIPTION OF THE PREFERRED EMBODIMENTS

The first process step of the bleaching, e.g. of an alkyl polyglycoside solution, preferably proceeds continuously in a stirred reactor, in a tubular reactor, in a combination thereof, or in a stirred-tank cascade. However, it is alternatively possible to bleach discontinuously in a stirred reactor (batch mode).

In the bleaching the concentration of the aqueous alkyl polyglycoside solution is 30 to 75 percent by weight. The amount of hydrogen peroxide used is 0.1 to 7, preferably 0.5 to 4, percent by weight (based on dry matter). The temperature in the bleaching is 40° to 95° C., temperatures of 50° to 80° C. being particularly preferred. The pH is 7 to 12, preferably 8 to 11, and the concentration of stabilizer (decomposition inhibitor) is 50 to 10,000, preferably 200 to 6,000, ppm (based on dry matter). The hydrogen peroxide stabilizers used are preferably inorganic magnesium compounds.

The second process step comprises the complete decomposition of the excess hydrogen peroxide and/or of the oxidizing secondary products formed therefrom using enzymes as catalyst.

The enzymatically catalyzed decomposition preferably proceeds continuously after addition of the enzyme, passing the material stream through a stirred reactor, a tubular reactor, a combination thereof, or a stirred-tank cascade. It is alternatively possible to carry out the catalyzed decomposition after enzyme addition in the product storage vessel. It is in addition alternatively possible to carry out only the secondary reaction to complete the degradation of the hydrogen peroxide and its secondary products in the product storage vessel. A different type of peroxide decomposition (e.g. using transition metals and/or transition metal compounds on a catalyst fixed bed) can be provided upstream of the enzymatically catalyzed decomposition.

The temperature in the enzymatic reaction is 10° to 80° C., preferably 20° to 60° C., and particularly preferably 30° to 50° C., depending on the enzyme used.

The pH is adjusted to 7 to 12, a pH of 7 to 10 being preferred.

The amount of enzyme depends on the enzyme activity. It can be from 0.1 to 5,000 ppm (based on the solutions), values between 1 and 2,000 ppm being preferred. It can be expedient to add the enzyme to the peroxide decomposition stage at one or a plurality of positions.

Examples of enzymes which can be mentioned are in particular catalases, glucose oxidases and superoxide dismutases.

The enzymes can also be used in stabilized or immobilized form.

The process has the following advantages:
the peroxide decomposition proceeds under mild conditions (no risk of product damage),
the decomposition reaction is easy to control (no vigorous frothing due to excessive oxygen evolution at the beginning),
short residence times are sufficient for complete peroxide decomposition under appropriate reaction conditions,
very low-odor products of extremely pale color are formed,
the products are reliably free of hydrogen peroxide and peroxide,
the products have high color stability on heating,
the process is generally applicable to surfactant solutions which are dark-colored due to their preparation, e.g. solutions of anionic surfactants (examples: paraffinsulphonates, α-sulpho fatty acid methyl esters) and non-ionic surfactants (example: alkyl polyglycoside(s)).

A continuous defoamer machine can be provided downstream of the first and/or second stage of the bleaching process, in which machine the alkyl polyglycoside(s) which is permeated by foam under some circumstances is compressed by centrifugation and is thus made more easily pumpable.

What is claimed as new and desired to be secured by Letters Patent of the United States is:

1. A process for bleaching a concentrated aqueous surfactant solution comprising:
    (1) adding a bleaching agent to said solution to bleach the surfactant solution, wherein the bleaching agent comprises hydrogen peroxide in the presence of a stabilizer,
    (2) optionally decomposing peroxide by contacting said solution with a transition metal and/or transition metal compound on a catalyst bed, and
    (3) decomposing excess unreacted hydrogen peroxide and/or oxidizing secondary products resulting therefrom by addition of a catalytic enzyme to said solution.

2. A process for bleaching an aqueous surfactant solution according to claim 1, wherein the surfactant is a non-ionic surfactant.

3. A process for bleaching an aqueous surfactant solution according to claim 1, wherein the surfactant is an alkyl polyglycoside.

4. A process for bleaching an aqueous surfactant solution according to claim 1, wherein the stabilizer comprises 50 to 10,000 ppm (based on surfactant) of an inorganic magnesium compound.

5. A process for bleaching an aqueous surfactant solution according to claim 1, wherein the enzyme comprises 0.1 to 5,000 ppm (based on surfactant) of a catalase.

6. A process for bleaching an aqueous surfactant solution according to claim 1, wherein the enzyme comprises 0.1 to 5,000 ppm (based on surfactant) of a glucose oxidase.

7. A process for bleaching an aqueous surfactant solution according to claim 1, wherein the enzyme comprises 0.1 to 5,000 ppm (based on surfactant) of a superoxide dismutase.

8. A process for bleaching an aqueous surfactant solution according to claim 1, wherein the enzyme is used in stabilized or immobilized form.

9. A process for bleaching an aqueous surfactant solution according to claim 1, wherein the temperature in the enzymatic decomposition is 10° to 80° C.

10. A process for bleaching an aqueous surfactant solution according to claim 1, wherein the temperature in the enzymatic decomposition is 20° to 60° C.

11. A process for bleaching an aqueous surfactant solution according to claim 1, wherein the temperature in the enzymatic decomposition is 30° to 50° C.

12. A process for bleaching an aqueous surfactant solution according to claim 1, wherein the pH during enzymatic decomposition is 7 to 12.

13. A process for bleaching an aqueous surfactant solution according to claim 1, wherein the pH during enzymatic decomposition is 7 to 10.

* * * * *